US012203960B2

(12) United States Patent
Lee et al.

(10) Patent No.: US 12,203,960 B2
(45) Date of Patent: Jan. 21, 2025

(54) MANUFACTURING FIXTURE AND PROCESS FOR ELECTRODE OF NEUROMODULATION PROBE

(71) Applicant: Industrial Technology Research Institute, Hsinchu (TW)

(72) Inventors: Jo-Ping Lee, Hsinchu (TW); Kun-Ta Wu, Nantou County (TW); Wei-Chin Huang, Tainan (TW); An-Li Chen, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 149 days.

(21) Appl. No.: 18/089,158

(22) Filed: Dec. 27, 2022

(65) Prior Publication Data

US 2023/0204627 A1    Jun. 29, 2023

Related U.S. Application Data

(60) Provisional application No. 63/294,173, filed on Dec. 28, 2021.

(30) Foreign Application Priority Data

Sep. 12, 2022   (TW) ................... 111134313

(51) Int. Cl.
*G01R 31/20*   (2006.01)
*G01R 1/067*   (2006.01)
*G01R 1/073*   (2006.01)

(52) U.S. Cl.
CPC ..... *G01R 1/07307* (2013.01); *G01R 1/06705* (2013.01)

(58) Field of Classification Search
CPC .. A61N 1/0529; A61N 1/0534; A61N 1/0553; A61N 1/0556; A61N 1/276; G01R 1/06705; G01R 1/06794; G01R 1/07307
See application file for complete search history.

(56) References Cited

U.S. PATENT DOCUMENTS 7,429,333 B2    9/2008  Chiou
11,040,193 B2*  6/2021  Schüttler ............. A61N 1/0551
(Continued)

FOREIGN PATENT DOCUMENTS

CN    204302417 U    4/2015
CN    105708491 B    11/2018
(Continued)

OTHER PUBLICATIONS

TW OA issued on Apr. 19, 2023.

*Primary Examiner* — Thang X Le
(74) *Attorney, Agent, or Firm* — WPAT, PC (57) ABSTRACT

A manufacturing process for electrode of neuromodulation probe includes the steps of: preparing a plurality of the manufacturing fixtures for electrode of neuromodulation probe; preparing a plurality of the manufacturing fixtures for electrode in a surrounding manner by having the first-layer frames to be externally disposed side by side with the bevels of the two neighboring first-layer frames close to each other, so that the second-layer frames, the plurality of electrodes and the plurality of wires are enclosed thereinside; placing a cylinder amid the plurality of manufacturing fixtures for electrode to have the plurality of wires to surround the cylinder; having a fluid plastic to surround the cylinder by filling all the spaces between the plurality of wires and the plurality of electrodes, and waiting the fluid plastic to cure; removing the plurality of first-layer frames and the plurality of second-layer frames; and, pulling off the cylinder.

23 Claims, 11 Drawing Sheets

(56) References Cited

U.S. PATENT DOCUMENTS

| | | | | |
|---|---|---|---|---|
| 2008/0027504 | A1* | 1/2008 | Bedenbaugh | A61N 1/0536 607/45 |
| 2011/0264178 | A1* | 10/2011 | Mehregany | A61N 1/0529 607/116 |
| 2018/0289949 | A1* | 10/2018 | Bachinski | A61B 18/1492 |
| 2020/0390363 | A1* | 12/2020 | Addison | A61B 5/0538 |
| 2022/0095979 | A1* | 3/2022 | Shimada | A61N 1/056 |
| 2022/0206083 | A1* | 6/2022 | Kaplan | A61N 1/08 |

FOREIGN PATENT DOCUMENTS

| | | |
|---|---|---|
| CN | 211213134 U | 8/2020 |
| TW | I287088 | 9/2007 |
| TW | 200829215 | 7/2008 |
| TW | 201113216 | 4/2011 |
| TW | I695174 | 11/2020 |

* cited by examiner

MANUFACTURING FIXTURE AND PROCESS FOR ELECTRODE OF NEUROMODULATION PROBE

CROSS REFERENCE TO RELATED APPLICATION

This application claims the benefits of provisional application Ser. No. 63/294,173, filed on Dec. 28, 2021, and Taiwan application serial No. 111134313, filed on Sep. 12, 2022. The disclosures of which are incorporated by references herein in its entirety.

TECHNICAL FIELD

The present disclosure relates in general to a medical technology, and more particularly to a manufacturing fixture and process for electrode of probe.

BACKGROUND

It is well known that the nuclei in the brain are connected by plural nerve fibers. By having the subthalamic neucleus (STN) as an example, in order to produce smooth movements, the subthalamic nucleus would generate electrical signals to activate the other nuclei (such as the globus pallidus interna, GPi) so as to promote the secretion of dopamine in the putamen for controlling initiation and/or cessation of the corresponding movements. If these neural networks fail to activate, clinical symptoms such as stiffness or tremors due to insufficient dopamine secretion would be formed finally to lead to Parkinson's disease.

In addition to medications for the aforesaid neural disorders, another approach is to implant neuromodulation probes. A typical neuromodulation probe is provided with a plurality of electrodes, and each of these electrode is connected to a wire. By providing relevant current to the electrode through the corresponding wire, the respective STN or GPi would be stimulated to activate the corresponding neural network and thus improve patient's movement disorder.

In the aforesaid therapy, in order to implant the tiny neuromodulation probe into the human brain, sizes of the electrodes and the wires for the neuromodulation probe shall be made extremely small, thus from which consistency of the electrodes would be a problem. As such, difficulty of assembling and manufacturing the electrodes of the neuromodulation probe would lead inevitable to less manufacturing accuracy and higher production cost.

For example, if a planar array is applied to assemble the electrodes, the resulted configuration is hard to provide a smooth surface, and the gaps thereof would be highly possible to cause inflammation and/or contamination.

In addition, if a semiconductor process is used, though the size of the electrodes can be small and the number thereof can be large, yet the investment on the materials and the process equipment would be expensive.

Accordingly, how to develop a "manufacturing fixture and process for electrode of neuromodulation probe" that can reduce the difficulty in fabricating the electrodes and the neuromodulation probes, improve the accuracy in assembling the electrodes, and reduce the manufacturing costs, without sacrificing the surface smoothness and causing the inflammation and contamination, is definitely an urgent problem to be solved by those skilled in the art.

SUMMARY

In one embodiment of this disclosure, a manufacturing fixture for electrode of neuromodulation probe includes:

a first-layer frame, having oppositely two lateral sides on an XY plane, the two lateral sides being parallel to each other and extending in an X direction, each of the two lateral sides having a bevel;

a plurality of electrodes, arranged in parallel to the XY plane and distributed along the X direction;

a second-layer frame, disposed between the first-layer frame and the plurality of electrodes, the second-layer frame having two opposite sides to connect the first-layer frame and the plurality of electrodes, respectively; and a plurality of wires, each of the plurality of wires being connected with a surface of one of the plurality of electrodes opposite to the second-layer frame.

In another embodiment of this disclosure, a manufacturing process for neuromodulation probe includes the steps of:

preparing a plurality of the manufacturing fixtures for electrode of neuromodulation probe;

preparing a plurality of the manufacturing fixtures for electrode in a surrounding manner by having the first-layer frames to be externally disposed side by side with the bevels of the two neighboring first-layer frames close to each other, so that the second-layer frames, the plurality of electrodes and the plurality of wires are enclosed thereinside;

placing a cylinder amid the plurality of manufacturing fixtures for electrode of neuromodulation probe to have the plurality of wires to surround the cylinder;

having a fluid plastic to surround the cylinder by filling all the spaces between the plurality of wires and the plurality of electrodes, and waiting the fluid plastic to cure;

removing the plurality of first-layer frames and the plurality of second-layer frames; and pulling off the cylinder.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
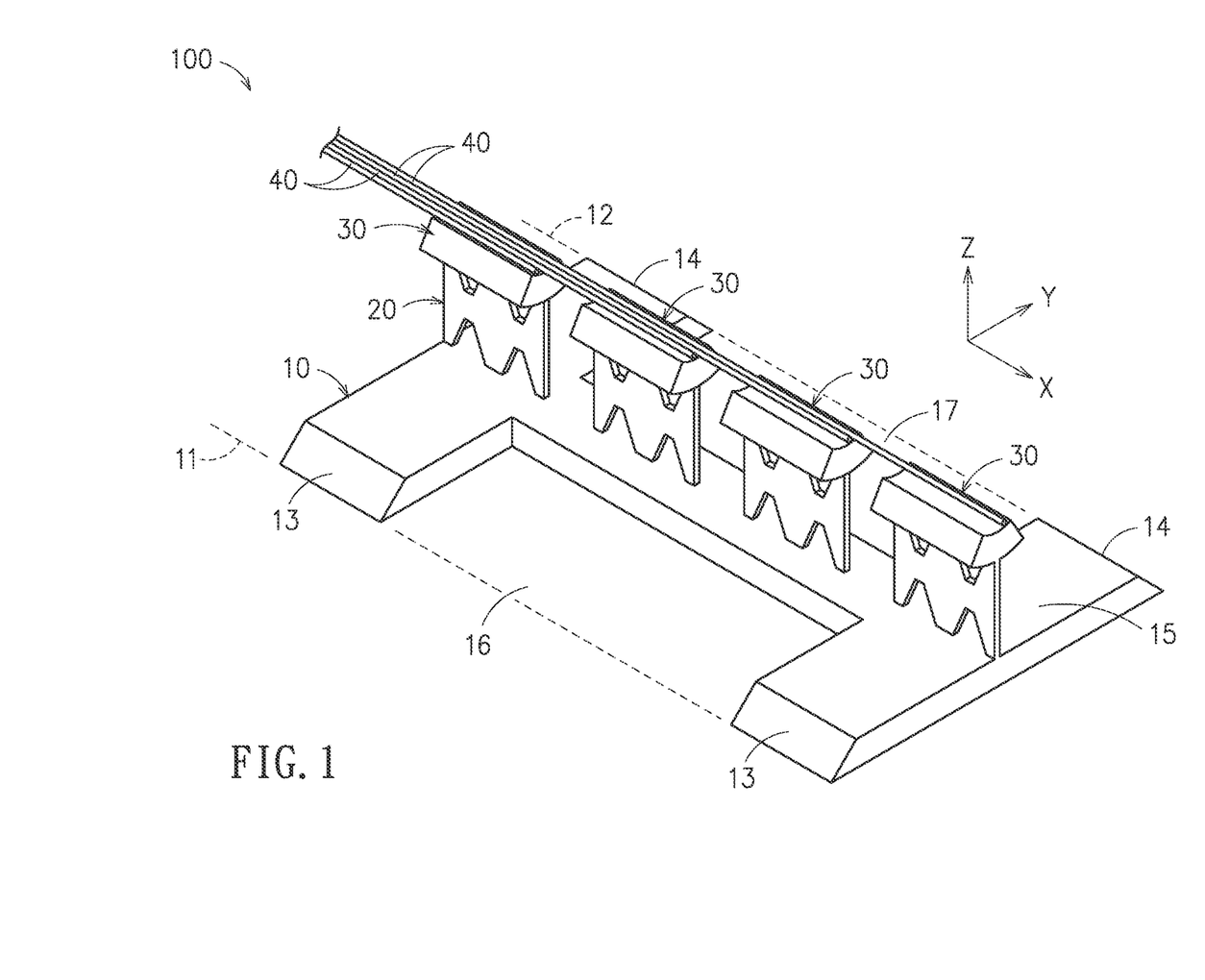
FIG. 1 is a schematic perspective view of an embodiment of the manufacturing fixture for electrode of neuromodulation probe in accordance with this disclosure.
Figure 2:
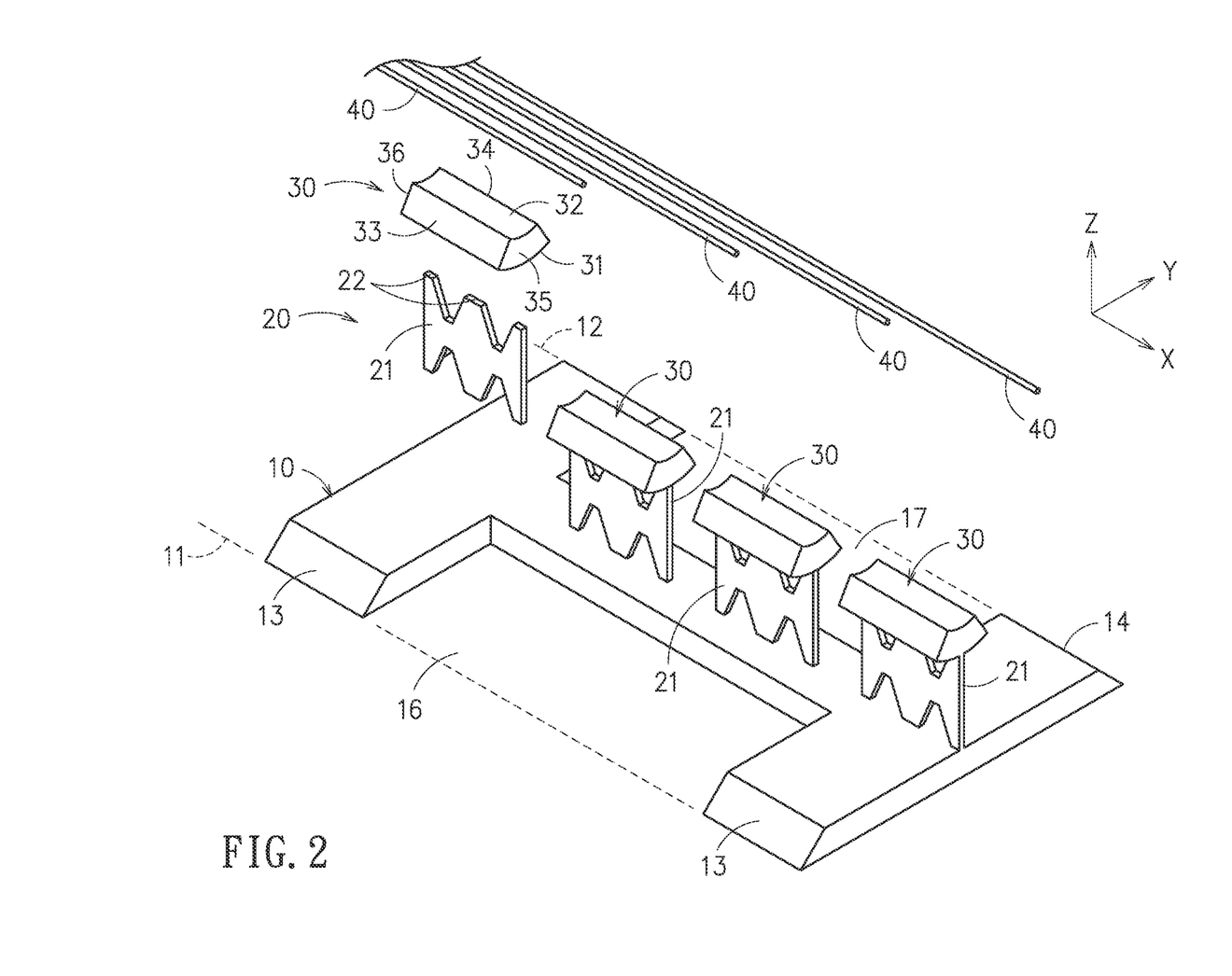
FIG. 2 is a schematic exploded view of FIG. 1.

Referring to FIG. 1 and FIG. 2, a manufacturing fixture 100 for electrode of neuromodulation probe of this disclosure includes a first-layer frame 10, a second-layer frame 20, a plurality of electrodes 30 and a plurality of wires 40.

Each of the first-layer frame 10, the second-layer frame 20 and the plurality of electrodes 30 can be manufactured as a unique piece by metallic printing.

The first-layer frame 10 has two opposite lateral sides 11, 12 on an XY plane thereof, each of the two lateral sides 11, 12 has a bevel 13, 14, respectively, and the two lateral sides 11, 12 are parallel to each other in an X direction.

Each of the bevels 13, 14 is formed by inclining from a top surface 15 of the first-layer frame 10 facing the second-layer frame 20 to the corresponding lateral side 11, 12 of the first-layer frame 10, and extending laterally along the respective lateral side 11, 12.

Figure 3A:
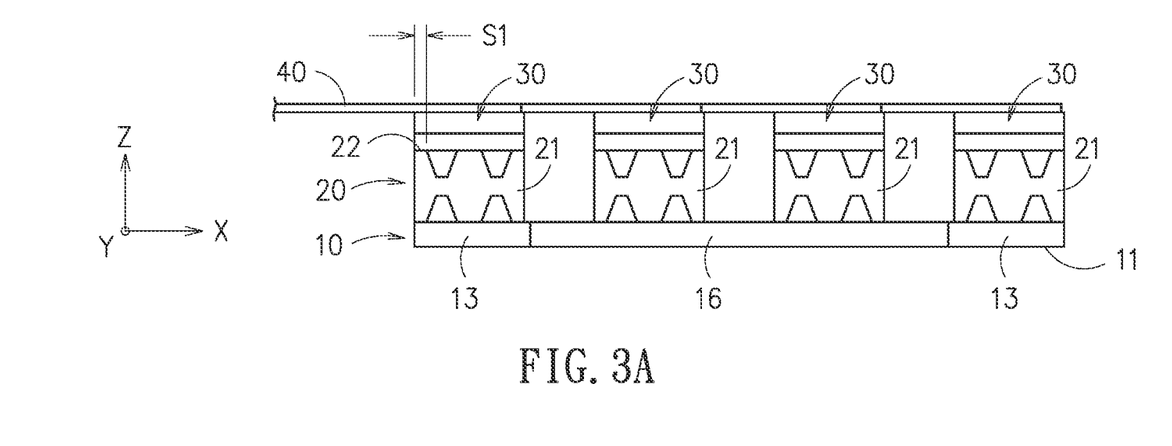
FIG. 3A is a schematic front view of FIG. 1.
Figure 3B:
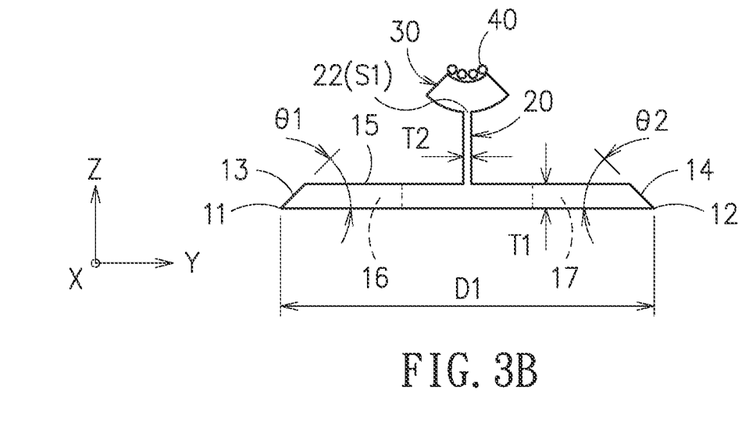
FIG. 3B is a schematic left-hand side of FIG. 1.
Figure 3C:
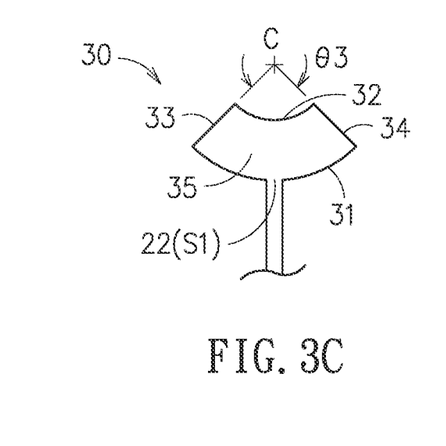
FIG. 3C is a schematic enlarged view of the electrode of FIG. 3B.

Referring now to FIG. 3A to FIG. 3C, the bevels 13, 14 of the corresponding lateral sides 11, 12 of the first-layer frame 10 are formed in individual tapers θ1, θ2 with respect to the same XY plane, and these two tapers θ1, θ2 are complementary angles. For example, the tapers θ1, θ2 can be 45° and 45°, 40° and 50°, or 30° and 60°, respectively.

In this disclosure, dimensions of the first-layer frame 10 are provided in accordance with practical requirements. For example, the first-layer frame 10 has a thickness T1 perpendicular to the XY plane and less than or equal to 1 mm, and a distance D1 between the two lateral sides 11, 12 of the first-layer frame 10 can be ranged between 1 mm and 10 mm.

Each of the lateral sides 11, 12 of the first-layer frame 10 is structured to have a middle recess portion 16, 17, such that a cross section of the first-layer frame 10 parallel to the XY plane would be formed in an H shape.

Referring to FIG. 3A to FIG. 3C, the second-layer frame 20, disposed between the first-layer frame 10 and the electrodes 30, has two opposite sides to connect the first-layer frame 10 and the electrodes 30, respectively.

The second-layer frame 20 is consisted of a plurality of connection units 21, and each of the connection units 21 is connected correspondingly with one of the electrodes 30.

In this disclosure, dimensions of the second-layer frame 20 are provided in accordance with practical requirements. For example, each of the connection units 21 of the second-layer frame 20 has a thickness T2 parallel to the XY plane and ranged between 1 mm and 5 mm; an outer diameter of a cross section S1, parallel to the XY plane, of a connection 22 interfacing the connection unit 21 of the second-layer frame 20 and the corresponding electrode 30 is ranged between 0.1 mm and 0.5 mm; and, the cross section S1, parallel to the XY plane, of the connection 22 interfacing the connection unit 21 of the second-layer frame 20 and the corresponding electrode 30 is shaped as a circle or a rectangle.

Referring to FIG. 2 and FIGS. 3A-3C, the plurality of electrodes 30 are arranged along the X direction by being parallel to the XY plane, and each of the electrodes 30 includes a first surface 31, a second surface 32, a third surface 33, a fourth surface 34, a fifth surface 35 and a sixth surface 36.

The first surface 31 is connected with the second-layer frame 20; the second surface 32 and the first surface 31 are oppositely disposed; the third surface 33 is disposed between the first surface 31 and the second surface 32; the fourth surface 34 and the third surface 33 are oppositely disposed between the first surface 31 and the second surface 32; the fifth surface 35 has four lateral sides to connect individually the first surface 31, the second surface 32, the third surface 33 and the fourth surface 34; the sixth surface 36 and the fifth surface 35 are oppositely disposed; and, the sixth surface 36 has four lateral sides to connect individually the first surface 31, the second surface 32, the third surface 33 and the fourth surface 34.

In the first surface 31, the two opposite sides thereof to connect the third surface 33 and the fourth surface 34 are parallel to each other, and also parallel to the X direction.

Referring to FIG. 3C, a cross section of the electrode 30 parallel to a YZ plane is shaped as a sector, in which the YZ plane is perpendicular to the XY plane. Practically, the fifth surface 35 and the sixth surface 36 can be also sector-shaped. The first surface 31 and the second surface 32 are convex surfaces with the same center C, and a distance between the first surface 31 and the center C is greater than that between the second surface 32 and the center C. An angle θ3 is formed between the third surface 33 and the fourth surface 34. In one exemplary example of this embodiment, the angle θ3 is less than 90°.

In this disclosure, dimensions of the electrode 30 are provided in accordance with practical requirements. For example, the distance (i.e., the radius) between the arc of the first surface 31 and the center C is greater than or equal to 0.5 mm, but less than or equal to 1.27 mm.

Referring to FIG. 1, FIG. 2, FIG. 3B and FIG. 3C, a surface (i.e., the second surface 32) of each of the electrodes 30 that opposite a surface (i.e., the first surface 31) connects the corresponding connection unit 21 of the second-layer frame 20 is connected with a wire 40. In this embodiment, the wire 40 is disposed on the second surface 32 of the electrode 30, and each of the electrodes 30 is connected with one wire 40. Dimensions of the wire 40 are determined according to practical requirements. For example, a diameter of the wire 40 can be ranged between 0.1 mm and 0.3 mm.

Referring to FIGS. 4A-4D, different stages in assembling the neuromodulation probe by using the manufacturing fixture 100 of FIG. 1 are demonstrated schematically and orderly. In particular, FIGS. 4A-4D for the manufacturing fixture 100 for electrode of neuromodulation probe are provided in lateral side views at specific angles.

Figure 4A:
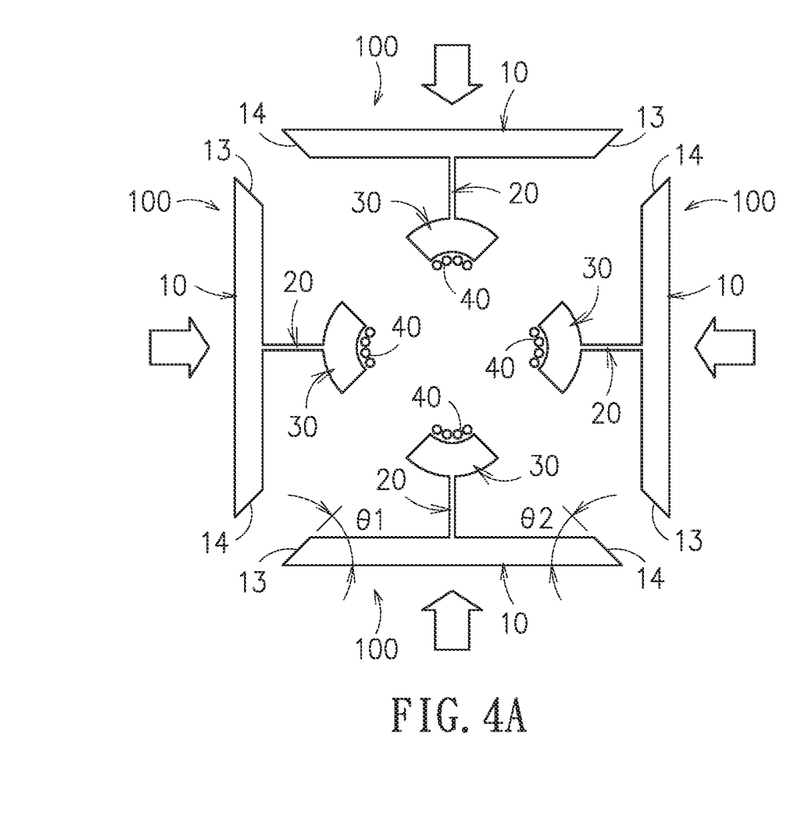
FIGS. 4A-4D demonstrate schematically and orderly different stages in assembling the neuromodulation probe of FIG. 1.

As shown in FIG. 4A, four manufacturing fixtures 100 for electrode of neuromodulation probe are prepared, and these four manufacturing fixtures 100 are arranged in a surrounding manner by having the first-layer frames 10 to be externally disposed side by side with the bevels 13, 14 of the two neighboring first-layer frames 10 close to each other. Thereupon, the second-layer frames 20, the plurality of electrodes 30 and the plurality of wires 40 are enclosed.

Figure 4B:
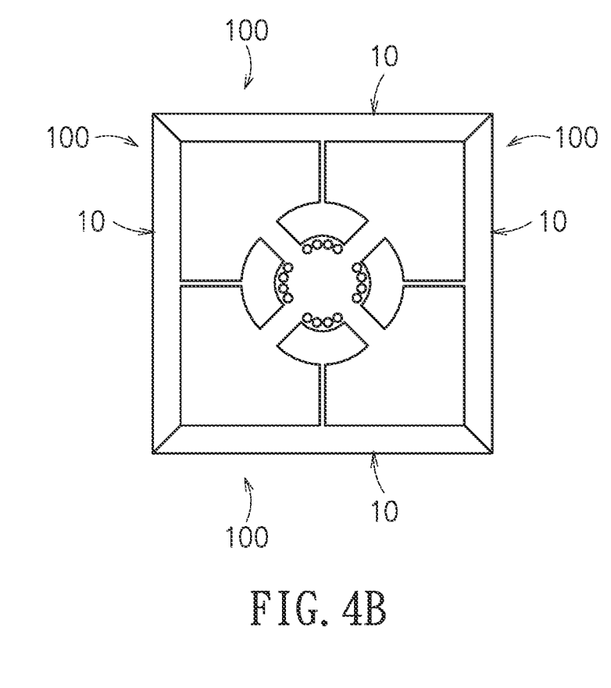

As shown in FIG. 4B, since the tapers θ1, θ2 of the bevels 13, 14 are complementary angles, thus these four first-layer frames 10 of the corresponding manufacturing fixtures 100 can be disposed into a rectangular form.

Figure 4C:
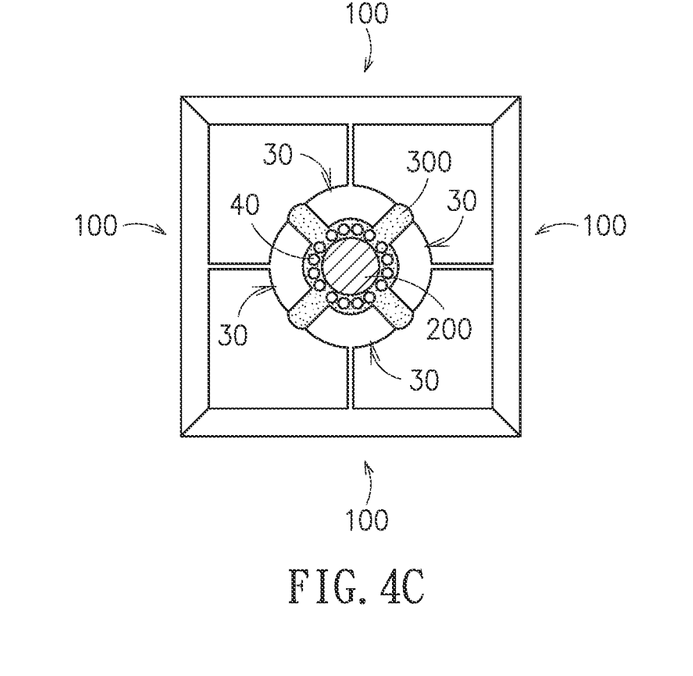

As shown in FIG. 4C, a cylinder 200 is placed amid the plurality of manufacturing fixtures 100 for electrode to have the plurality of wires 40 to surround the cylinder 200. In this embodiment, the cylinder 200 can be a solid or hollow structure.

Then, a fluid plastic 300 is introduced to fill all the spaces between the wires 40 and the electrodes 30 so as to surround the cylinder 200 externally, and then the fluid plastic 300 is there to cure. In this embodiment, the fluid plastic 300 can be one of silicone, PP, PE and PEG.

Figure 4D:
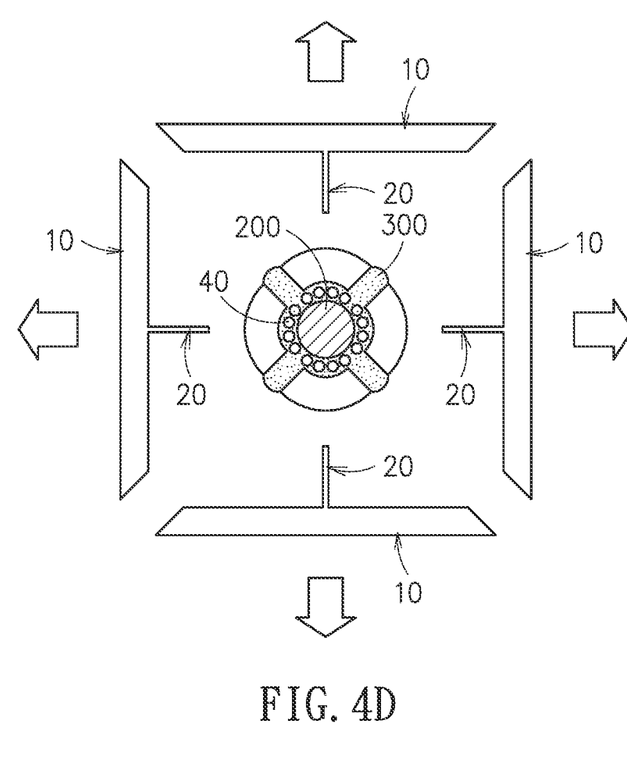

As shown in 4D, the first-layer frames 10 and the second-layer frames 20 can be simultaneously removed by appropriate cutting, grinding or any means the like. At the same time, the entire surface can be polished. After the cutting, the first-layer frames 10 and the second-layer frame 20 can be recycled through a thermal melting means. In one embodiment, since the final step of the manufacturing process would separate the plurality of electrodes 30 off the second-layer frame 20, thus the cross section S1 (parallel to the XY plane) of the connection 22 of the second-layer frame 20 and each of the electrodes 30 may be less than or equal to the maximum cross-sectional area of the second-layer frame 20 on the XY plane, such that the cut-to-separate process can be easier.

Figure 5:
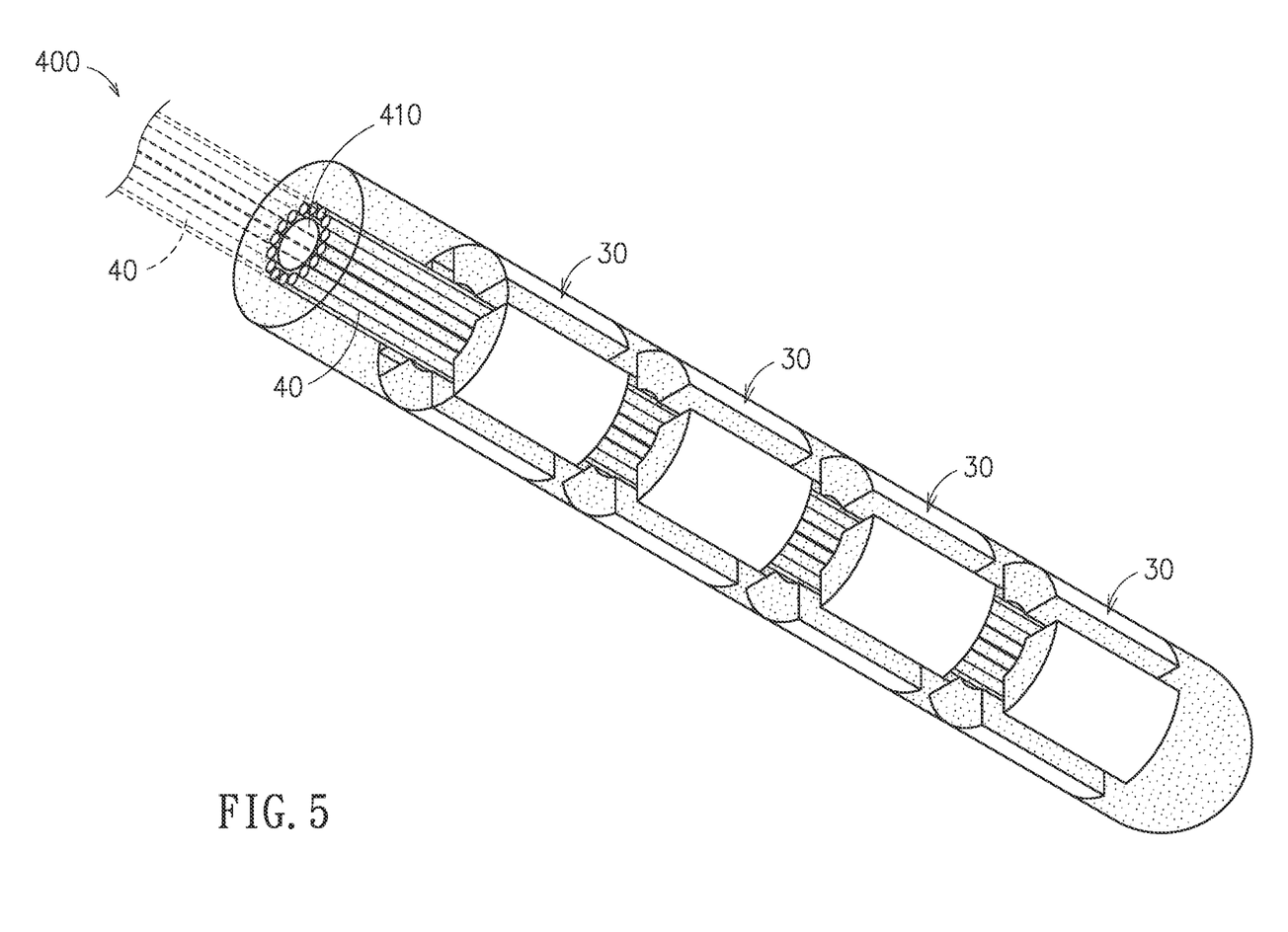
FIG. 5 is a schematic perspective view of a neuromodulation probe produced by the embodiment of FIG. 1.

Finally, the central cylinder 200 is retrieved off, such that the aspect of the neuromodulation probe 400 shown in FIG. 5 can be achieved.

Referring to FIG. 5, the neuromodulation probe 400 is extended longitudinally, and has a central tunnel 410 for receiving a tool. The neuromodulation probe 400 has four sets of the electrodes 30, each set thereof is consisted of four electrodes 30, and thus total 16 electrodes 30 are included in the neuromodulation probe 400. Each of the electrodes 30 is connected with a wire 40 extending out of the neuromodulation probe 400. It is noted that the portion of each wire 40 out of the neuromodulation probe 400 is presented in dashed lines in FIG. 5.

In producing the neuromodulation probe 400, a polishing step shall be included to provide a smooth surface, such that, while the neuromodulation probe 400 is implanted in human body, inflammation and contamination won't be caused at the wounded skin.

Figure 6:
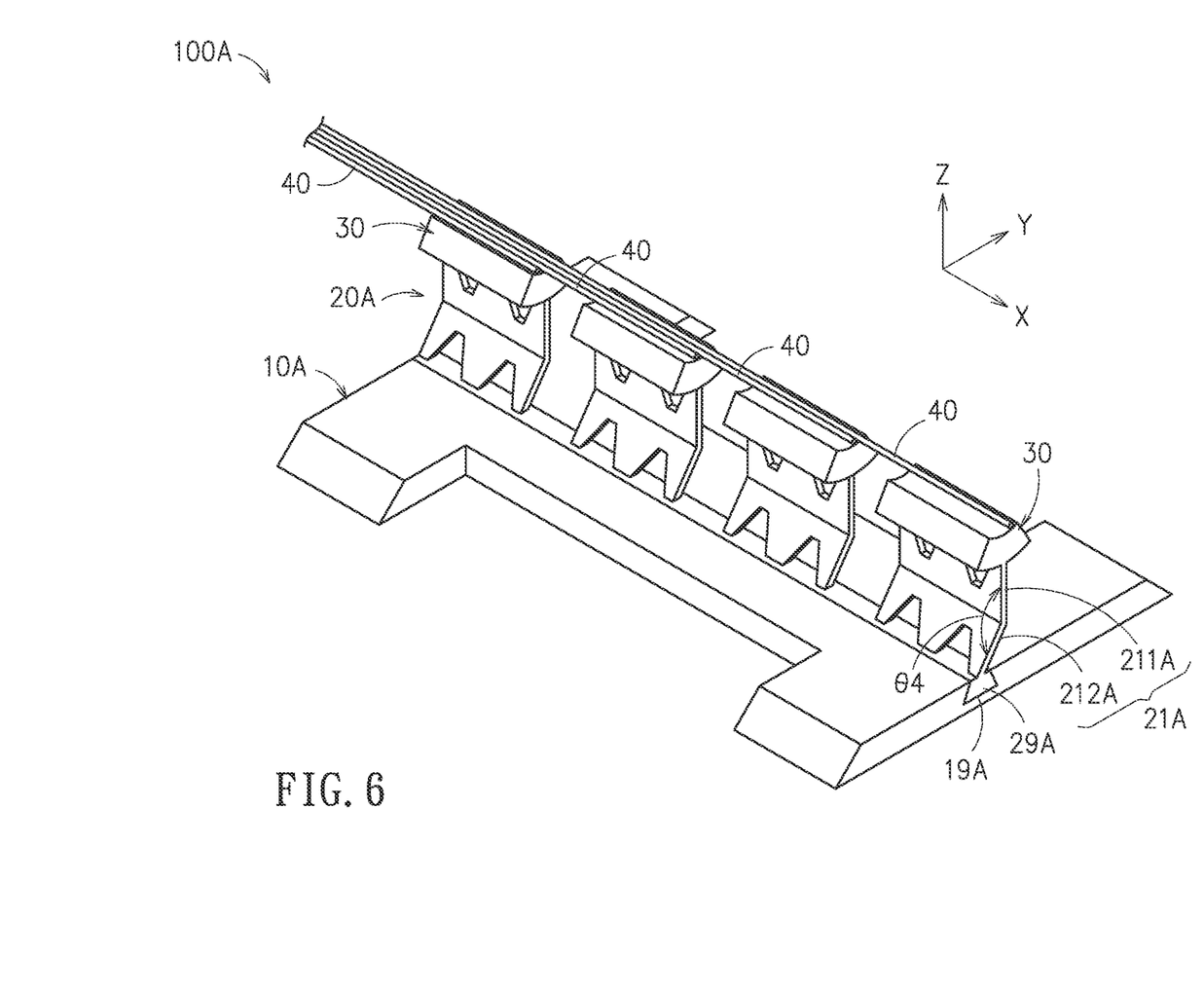
FIG. 6 is a schematic perspective view of another embodiment of the manufacturing fixture for electrode of neuromodulation probe in accordance with this disclosure.
Figure 7:
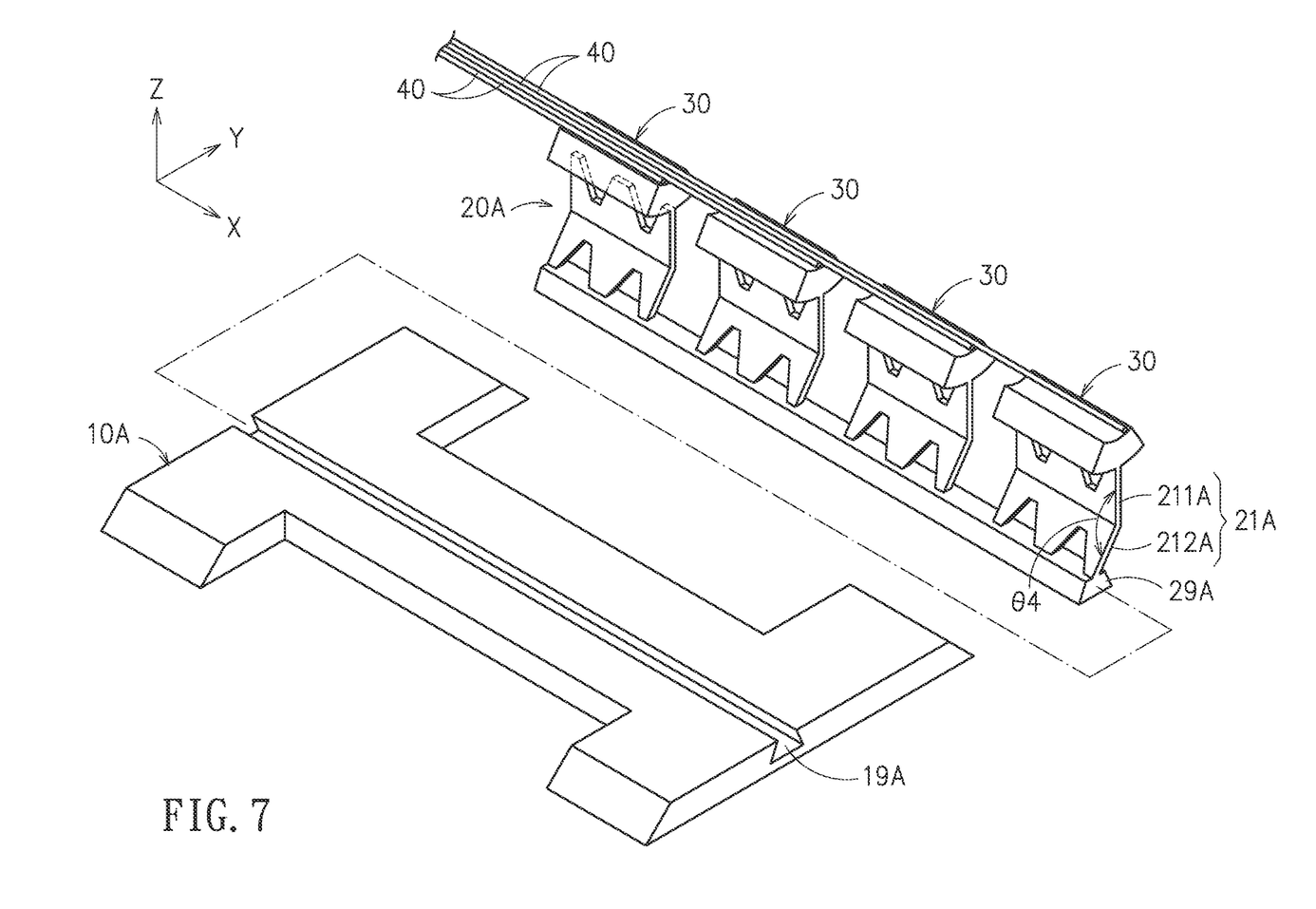
FIG. 7 is a schematic exploded view of FIG. 6.

Referring to FIG. 6 and FIG. 7, another embodiment of the manufacturing fixture 100A for electrode of neuromodulation probe is schematically shown. In this embodiment, the manufacturing fixture 100A includes a first-layer frame 10A, a second-layer frame 20A, a plurality of electrodes 30 and a plurality of wires 40.

It is noted that, in this embodiment, the first-layer frame 10A and the second-layer frame 20A are detachably connected.

The first-layer frame 10A is furnished with a dovetail groove 19A extending along the X direction, and the second-layer frame 20A is furnished correspondingly with a dovetail end 29A extending along the X direction to engage slidably the dovetail end 19A.

In addition, the second-layer frame 20A is consisted of a plurality of connection units 21A, and each of the connection units 21A is connected with one said electrode 30.

Each of the connection units 21A includes a first connection plate 211A and a second connection plate 212A. The first connection plate 211A is formed by protruding vertically downward by a predetermined length from a bottom of the corresponding electrode 30, i.e., by being perpendicular to the XY plane. Two opposite ends of the first connection plate 211A are connected with the corresponding electrode 30 and the second connection plate 212A, respectively. Two opposite ends of the second connection plate 212A are connected with the first connection plate 211A and the dovetail end 29A, respectively.

An angle θ4 is formed between the first connection plate 211A and the second connection plate 212A. For example, the angle θ4 is ranged between 90° and 180°.

Referring to FIGS. 8A-8D, different stages in assembling the neuromodulation probe by using the manufacturing fixture 100A of FIG. 6 are demonstrated schematically and orderly. In particular, FIGS. 8A-8D for the manufacturing fixture 100A for electrode are provided in lateral side views at specific angles.

Figure 8A:
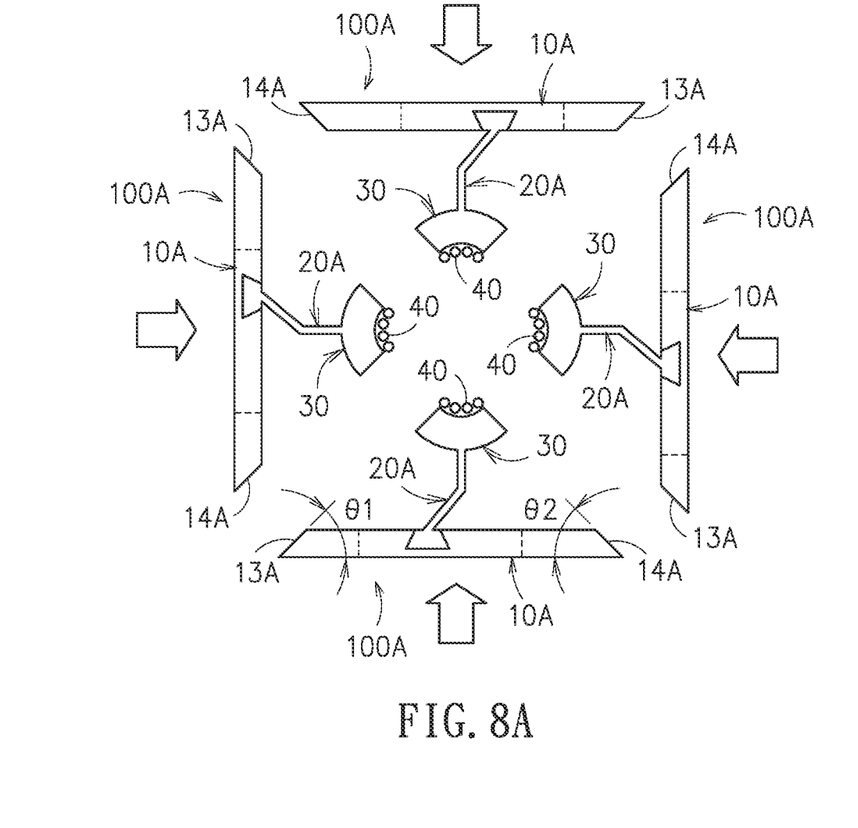
FIGS. 8A-8D demonstrate schematically and orderly different stages in assembling the neuromodulation probe of FIG. 6.

Referring to FIG. 8A, four manufacturing fixtures 100A for electrode are prepared, and these four manufacturing fixtures 100A are arranged in a surrounding manner by having the first-layer frames 10A to be externally disposed side by side with the bevels 13A, 14A of the two neighboring first-layer frames 10A close to each other. Thereupon, the second-layer frames 20A, the plurality of electrodes 30 and the plurality of wires 40 can be enclosed.

Figure 8B:
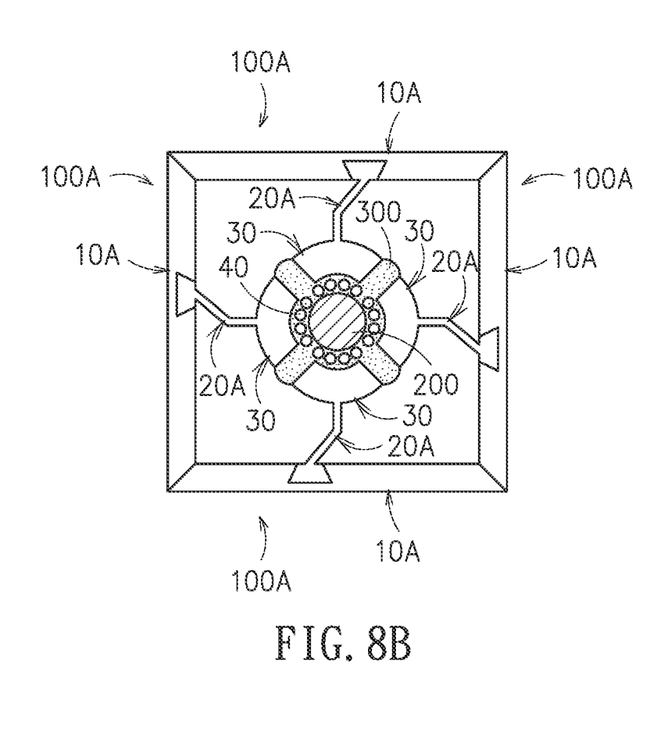

As shown in FIG. 8B, since the tapers θ1, θ2 of the bevels 13A, 14A are complementary angles, thus these four first-layer frames 10A of the corresponding manufacturing fixtures 100A can be disposed into a rectangular form.

A cylinder 200 is placed amid the plurality of manufacturing fixtures 100A for electrode to have the plurality of wires 40 to surround the cylinder 200.

Then, a fluid plastic 300 is introduced to fill all the spaces between the wires 40 and the electrodes 30 so as to surround the cylinder 200 externally, and then the fluid plastic 300 is there to cure.

Figure 8C:
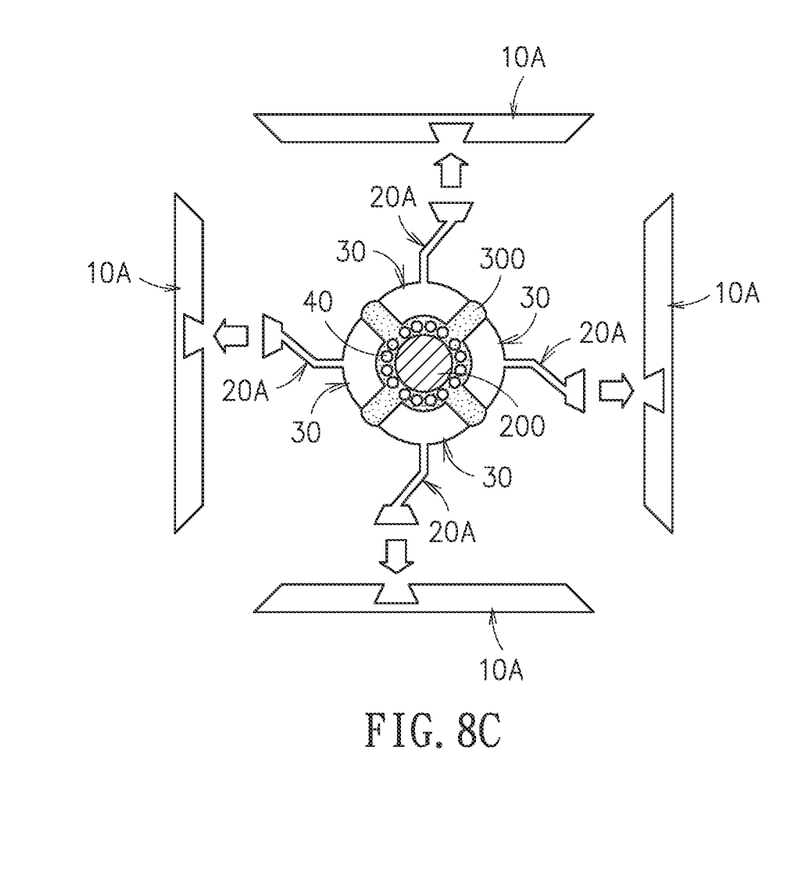
Figure 8D:
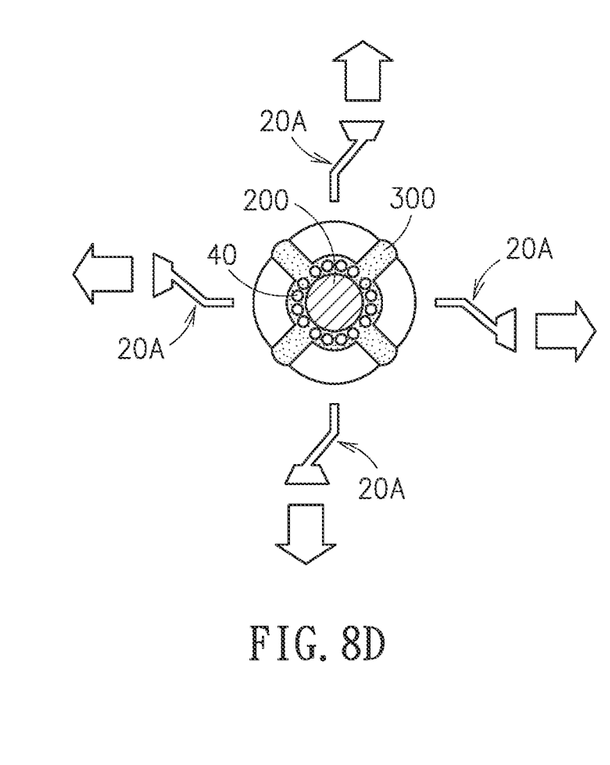

Referring to FIG. 8C and FIG. 8D, the first-layer frames 10A and the second-layer frames 20A can be removed. Since the first-layer frame 10A and the corresponding second-layer frame 20A are detachably engaged, thus the first-layer frame 10A is firstly pulled off, and then the second-layer frame 20A is removed by cutting or grinding. Simultaneously, a polishing step can be applied to the entire surface of the remaining. The pulled-off first-layer frames 10A can be reused, and the cut-out second-layer frames 20A can be recycled through a thermal melting means.

Then, the central cylinder 200 is pulled off to provide the neuromodulation probe 400 as shown in FIG. 5.

Though four manufacturing fixtures for electrode are introduced to surround and thus produce the neuromodulation probe in each of the aforesaid embodiments, yet the number of the manufacturing fixtures in this disclosure is not limited thereto. In some other embodiments, two, three or even more manufacturing fixtures for electrode can be applied to surround and produce the neuromodulation probe.

Referring to FIGS. 4A-4D and FIG. 9, according to this disclosure, a manufacturing process of neuromodulation probe 900 can include the following steps.

Figure 9:
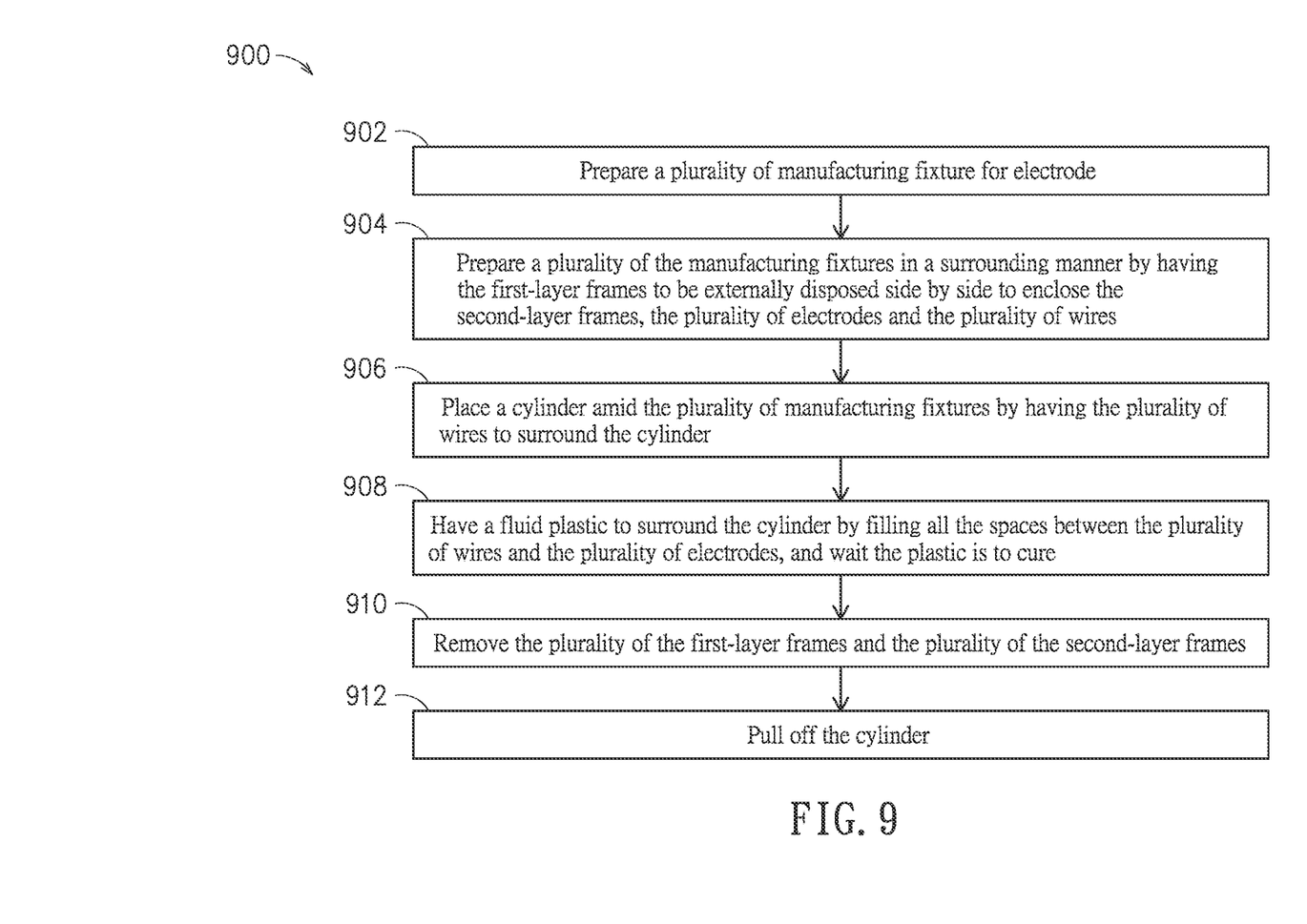
FIG. 9 is a schematic flowchart of an embodiment of the manufacturing process for electrode of neuromodulation probe in accordance with this disclosure.

Step 902: prepare a plurality of manufacturing fixture 100 for electrode.

Step 904: Prepare a plurality of the manufacturing fixtures 100 for electrode in a surrounding manner by having the first-layer frames 10 to be externally disposed side by side with the bevels 13, 14 of the two neighboring first-layer frames 10 close to each other. Thereupon, the second-layer frames 20, the plurality of electrodes 30 and the plurality of wires 40 can be enclosed.

Step 906: Place a cylinder 200 amid the plurality of manufacturing fixtures 100 for electrode by having the plurality of wires 40 to surround the cylinder 200.

Step 908: Have a fluid plastic 300 to surround the cylinder 200 by filling all the spaces between the plurality of wires 40 and the plurality of electrodes 30, and the plastic is waited to cure.

Step 910: Remove the plurality of the first-layer frames 10 and the plurality of the second-layer frames 20.

Step 912: Pull off the cylinder 200.

The aforesaid steps are also applicable to the embodiment of the manufacturing fixture 100A for electrode shown in FIGS. 8A-8D for preparing the neuromodulation probe.

In summary, with the manufacturing fixture and process for electrode of neuromodulation provided in this disclosure, a plurality of electrodes are formed on a two-layer structure to configure the manufacturing fixture for electrode, then a plurality of the manufacturing fixtures for electrode are arranged in a surrounding manner for filling thereinside with a plastic, these two-layer structures are then removed after the plastic is cured, and thus a neuromodulation probe can be obtained. Thereupon, the difficulty in producing the electrodes can be reduced, but the accuracy in assembling the electrodes would be elevated. In addition, since the two-layer structure can be recycled or reused, thus the production cost can be lowered. Further, through a polishing process, the neuromodulation probe can be finished with a smooth surface, from which possible inflammation and contamination can be avoided.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A manufacturing fixture for an electrode of a neuromodulation probe, comprising:
   a first-layer frame having oppositely two lateral sides on an XY plane, the two lateral sides being parallel to each other and extending in an X direction, and each of the two lateral sides having a bevel;
   a plurality of electrodes arranged in parallel to the XY plane and distributed along the X direction;
   a second-layer frame disposed between the first-layer frame and the plurality of electrodes, the second-layer frame having two opposite sides to connect the first-layer frame and the plurality of electrodes, respectively; and
   a plurality of wires, each of the plurality of wires being connected with a surface of one of the plurality of electrodes opposite to the second-layer frame.

2. The manufacturing fixture for the electrode of the neuromodulation probe of claim 1, wherein the bevel is extended along the corresponding lateral side, and formed by inclining from a top surface of the first-layer frame facing the second-layer frame to the corresponding lateral side.

3. The manufacturing fixture for the electrode of the neuromodulation probe of claim 1, wherein the first-layer frame has two said bevels at the two lateral sides thereof, the two bevels have individual tapers with respect to the XY plane, and the two tapers are complementary angles.

4. The manufacturing fixture for the electrode of the neuromodulation probe of claim 1, wherein the first-layer frame has two opposite recess portions disposed respectively at the two lateral sides, and a cross section of the first-layer frame parallel to the XY plane is shaped as an H.

5. The manufacturing fixture for the electrode of the neuromodulation probe of claim 1, wherein the second-layer frame includes a plurality of connection units, and each of the plurality of connection units is connected with one of the plurality of electrodes.

6. The manufacturing fixture for the electrode of the neuromodulation probe of claim 5, wherein an outer diameter of a cross section, parallel to the XY plane, of a connection interfacing one of the plurality of connection units of the second-layer frame and the corresponding electrode is ranged between 0.1 mm and 0.5 mm.

7. The manufacturing fixture for the electrode of the neuromodulation probe of claim 1, wherein a cross section, parallel to the XY plane, of a connection interfacing the second-layer frame and one of the plurality of electrodes is shaped as a circle or a rectangle.

8. The manufacturing fixture for the electrode of the neuromodulation probe of claim 1, wherein the electrode includes:
   a first surface connected with the second-layer frame;
   a second surface disposed oppositely to the first surface;
   a third surface disposed between the first surface and the second surface;
   a fourth surface disposed oppositely to the third surface and between the first surface and the second surface;
   a fifth surface having four sides to connect the first surface, the second surface, the third surface and the fourth surface, respectively; and
   a sixth surface disposed oppositely to the fifth surface, having another four sides to connect the first surface, the second surface, the third surface and the fourth surface, respectively.

9. The manufacturing fixture for the electrode of the neuromodulation probe of claim 8, wherein two opposite lateral sides of the first surface, connecting the third surface and the fourth surface, are parallel to each other in the X direction.

10. The manufacturing fixture for the electrode of the neuromodulation probe of claim 8, wherein a cross section of one of the plurality of electrodes, parallel to a YZ plane perpendicular to the XY plane, is shaped to be a sector, the first surface and the second surface are both convex with the same center, a distance between the first surface and the center is greater than another distance between the second surface and the center, and an angle is formed between the third surface and the fourth surface.

11. The manufacturing fixture for the electrode of the neuromodulation probe of claim 10, wherein the distance between the first surface and the center is greater than or equal to 0.5 mm, but less than or equal to 1.27 mm.

12. The manufacturing fixture for the electrode of the neuromodulation probe of claim 10, wherein the angle is less than 90°.

13. The manufacturing fixture for the electrode of the neuromodulation probe of claim 1, wherein a thickness of the first-layer frame perpendicular to the XY plane is less than or equal to 1 mm.

14. The manufacturing fixture for the electrode of the neuromodulation probe of claim 1, wherein a thickness of the second-layer frame parallel to the XY plane is ranged between 1 mm and 5 mm.

15. The manufacturing fixture for the electrode of the neuromodulation probe of claim 1, wherein a distance between the two opposite lateral sides of the first-layer frame is ranged between 1 mm and 10 mm.

16. The manufacturing fixture for the electrode of the neuromodulation probe of claim 1, wherein a diameter of one of the plurality of wires is ranged between 0.1 mm and 0.3 mm.

17. The manufacturing fixture for the electrode of the neuromodulation probe of claim 1, wherein the first-layer frame and the second-layer frame are detachably connected.

18. The manufacturing fixture for the electrode of the neuromodulation probe of claim 17, wherein the first-layer frame has a dovetail groove extending in the X direction, and the second-layer frame has a dovetail end extending in the X direction to engage the dovetail groove.

19. The manufacturing fixture for the electrode of the neuromodulation probe of claim 18, wherein the second-layer frame includes a plurality of connection units, each of the plurality of connection units is connected with one of the plurality of electrodes, each of the plurality of connection units includes a first connection plate and a second connection plate, two opposite ends of the first connection plate are connected respectively with one of the plurality of electrodes and the second connection plate, two opposite ends of the second connection plate are connected respectively with the first connection plate and the dovetail end, an angle is formed between the first connection plate and the second connection plate, and the angle is ranged between 90° and 180°.

20. The manufacturing fixture for the electrode of the neuromodulation probe of claim 19, wherein the first connection plate is protruded vertically downward by a predetermined length from a bottom of one of the plurality of the electrodes.

21. A manufacturing process for a neuromodulation probe, comprising the steps of:
preparing a plurality of the manufacturing fixtures for the electrode of the neuromodulation probe of claim 1;
preparing a plurality of the manufacturing fixtures for electrode of neuromodulation probe in a surrounding manner by having the first-layer frames to be externally disposed side by side with the bevels of the two neighboring first-layer frames close to each other, so that the second-layer frames, the plurality of electrodes and the plurality of wires are enclosed thereinside;
placing a cylinder amid the plurality of manufacturing fixtures for electrode of neuromodulation probe to have the plurality of wires to surround the cylinder;
having a fluid plastic to surround the cylinder by filling all the spaces between the plurality of wires and the plurality of electrodes, and waiting the fluid plastic to cure;
removing the plurality of first-layer frames and the plurality of second-layer frames; and
pulling off the cylinder.

22. The manufacturing process for the neuromodulation probe of claim 21, wherein the first-layer frame, the plurality of electrodes and the second-layer frame are all produced by metal printing.

23. The manufacturing process for the neuromodulation probe of claim 21, wherein the plurality of first-layer frames and the plurality of second-layer frames are removed by cutting or grinding.

* * * * *